(12) United States Patent
Paci et al.

(10) Patent No.: US 8,281,660 B2
(45) Date of Patent: Oct. 9, 2012

(54) INTEGRATED TORSIONAL-MICROBALANCE DEVICE IN MEMS TECHNOLOGY AND FABRICATION PROCESS THEREOF

(75) Inventors: Dario Paci, Leghorn (IT); Francesco Pieri, Pisa (IT); Pietro Toscano, Pisa (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 390 days.

(21) Appl. No.: 12/634,579

(22) Filed: Dec. 9, 2009

(65) Prior Publication Data

US 2010/0154544 A1 Jun. 24, 2010

(30) Foreign Application Priority Data

Dec. 9, 2008 (IT) ................................ TO2008A0916

(51) Int. Cl.
*G01H 13/00* (2006.01)
(52) U.S. Cl. ............................................ 73/580; 73/579
(58) Field of Classification Search .................... 73/580, 73/579, 649; 257/414, 415
See application file for complete search history.

(56) References Cited

U.S. PATENT DOCUMENTS

| | | | |
|---|---|---|---|
| 6,438,458 B2 * | 8/2002 | Shimoike et al. | 700/250 |
| 7,221,241 B2 * | 5/2007 | Lutz et al. | 333/186 |
| 7,459,099 B2 * | 12/2008 | Kubena et al. | 216/57 |
| 7,681,433 B2 * | 3/2010 | Konno et al. | 73/24.06 |
| 7,802,356 B1 * | 9/2010 | Chang et al. | 29/594 |
| 7,930,923 B2 * | 4/2011 | Patel et al. | 73/23.34 |
| 8,161,803 B2 * | 4/2012 | Oh et al. | 73/81 |

FOREIGN PATENT DOCUMENTS

| | | |
|---|---|---|
| WO | 98/50773 A2 | 11/1998 |
| WO | 02/12443 A2 | 2/2002 |
| WO | 2006/107961 A2 | 10/2006 |

OTHER PUBLICATIONS

Hierlemann, A. et al., "Microfabrication Techniques for Chemical/Biosensors," Proceedings of the IEEE 91(6):839-863, Jun. 2003.
Ismail, A.K. et al., "The Fabrication, Characterization and Testing of a MEMS Circular Diaphragm Mass Sensor," Journal of Micromechanics & Microengineering 18(2):25021, 1-10, Feb. 1, 2008.
Khuri-Yakub, B.T., "The Capacitive Micromachined Ultrasonic Transducer (CMUT) as a Chem/Bio Sensor," IEEE Ultrasonics Symposium 2007, New York, Oct. 28-21, 2007, pp. 472-475.
Lang, H.P. et al., "Cantilever Array Sensors," Materials Today 8(4):30-36, Apr. 2005.

(Continued)

*Primary Examiner* — J M Saint Surin
(74) *Attorney, Agent, or Firm* — Seed IP Law Group PLLC

(57) ABSTRACT

A MEMS microbalance that includes a substrate made of semiconductor material with a cavity, and a resonator, which is suspended above the cavity of the substrate and is formed by a mobile body, by at least one first arm connected between the substrate and the mobile body, which has a first thickness and which enables oscillations of the mobile body with respect to the substrate, by an actuation transducer connected to the mobile body for generating the oscillations at a resonance frequency, and by a detection transducer for detecting a variation of the resonance frequency, wherein the mobile body possesses at least one thin portion having a second thickness smaller than the first thickness of the first arm.

24 Claims, 13 Drawing Sheets

OTHER PUBLICATIONS

Lange, D. et al., "CMOS Resonant Beam Gas Sensing System with On-Chip Self Excitation," The 14th IEEE International Conference on Micro Electro Mechanical Systems (MEMS) 2001, Interlaken, Switzerland, Jan. 21-25, 2001, pp. 547-552.

Nannini, A. et al., "A CMOS-Compatible Bulk Technology for the Fabrication of Magnetically Actuated Microbalances for Chemical Sensing," Sensors and Actuators B: Chemical 118(1-2):343-348, Oct. 2006.

Paci, D. et al., "A CMOS-Compatible, Magnetically Actuated Resonator for Mass Sensing Applications," Sensors and Actuators B: Chemical 129(1):10-17, Jan. 2008.

Suarez, G. et al., "Direct Adsorption of Chemically Modified Biomolecules Onto Gold: A Rapid Method for Biological Functionalization of MEMS," Seminar on MEMS Sensors and Actuators 2006, The Institute of Engineering and Technology, London, Apr. 28, 2006, pp. 113-118.

Voiculescu, I. et al., "Electrostatically Actuated Resonant Microcantilever Beam in CMOS Technology for the Detection of Chemical Weapons," IEEE Sensors Journal 5(4):641-647, Aug. 2005.

* cited by examiner

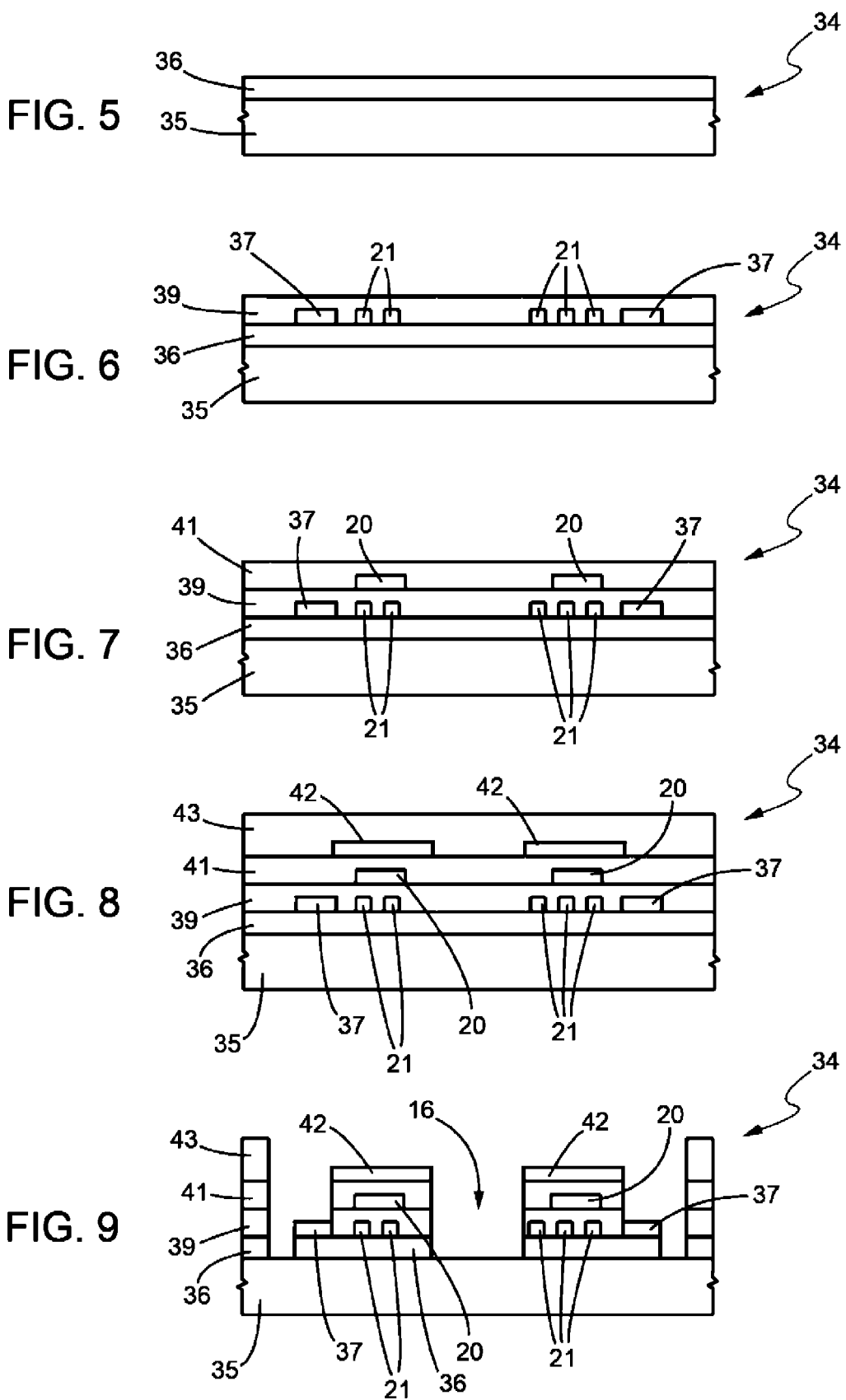

INTEGRATED TORSIONAL-MICROBALANCE DEVICE IN MEMS TECHNOLOGY AND FABRICATION PROCESS THEREOF

BACKGROUND

1. Technical Field

The present disclosure relates to an integrated torsional-microbalance device in MEMS technology and to a corresponding fabrication process.

2. Description of the Related Art

A microbalance, typically obtained with MEMS technology, is a mechanical structure driven by an electrical signal that causes an oscillatory movement thereof, preferably at the resonance frequency of the mechanical structure. FIG. 1 shows a block diagram of a control system 1 of a known type used for actuating a microbalance. The control system 1 comprises a first transducer 2, which receives on an input of its own a driving signal $V_{in}$ generated by an appropriate driving electronics 4 and, on the basis of the driving signal $V_{in}$ received, generates a force F on a microbalance 10, such as to cause oscillation preferably at a resonance frequency $f_0$, specific for the mechanical structure of the microbalance 10. External events, such as, for example, a change in the mass of the microbalance 10 due to deposition of material M on the microbalance 10, cause a shift $\Delta f_0$ of the frequency of oscillation from the resonance frequency $f_0$. A second transducer 3 converts the oscillations of the microbalance 10 into an electrical signal, generating at output an output signal $V_o$ that varies in a way depending upon the frequency of oscillation of the microbalance 10. The output signal $V_o$ is then supplied to a processing electronics 5 for subsequent processing steps.

FIGS. 2 and 3 show, respectively in top plan view and in perspective view, a possible embodiment of the microbalance 10 and of part of the control system 1 (the driving electronics 4 for generating the driving signal $V_{in}$ and the processing electronics 5 for processing the output signal $V_o$ are not shown). The control system 1 of this type, together with the microbalance 10, is described, for example, in "A CMOS-compatible bulk technology for the fabrication of magnetically actuated microbalances for chemical sensing", A. Nannini, D. Paci, F. Pieri, P. Toscano, Sensors and Actuators B, vol. 118, pp. 343-348, 2006, and in "A CMOS-compatible, magnetically actuated resonator for mass sensing applications", D. Paci, F. Pieri, P. Toscano, A. Nannini, Sensors and Actuators B, vol. 129, pp. 10-17, 2008.

With joint reference to FIGS. 2 and 3, the microbalance 10 comprises a mobile body 11, including a main portion 17 preferably of a square or rectangular shape, supported by a first arm 12 and by a second arm 13. The first and second arms 12, 13 possess a respective end that is fixed with respect to the main portion 17, whilst the other end is fixed with respect to a substrate 14. The first and the second arms 12, 13 are moreover aligned along an axis of symmetry 15 passing through the centroid of the mobile body 11.

The mobile body 11 possesses at least one opening 16, preferably of a square or rectangular shape and having its own centroid set on the axis of symmetry 15. The opening 16 has the function, during the steps of fabrication of the microbalance 10 (as will be described better in what follows), of enabling removal of the underlying layer/layers of material (for example, the substrate 14) and providing a suspended structure, supported by the first and second arms 12, 13.

The mobile body 11 further comprises an actuation winding 20 and a detection winding 21, integrated in the mobile body 11 on different metal levels (for example, the detection winding 21 is formed on a first metal level, and the actuation winding 20 on a second metal level, or vice versa). The actuation winding 20 comprises a first connection portion 20' and an actuation loop 20", both of which are made of conductive material and are electrically connected to one another, whilst the detection winding 21 comprises a second connection portion 21' and a plurality of concentric detection loops 21", all of which are made of conductive material and are electrically connected to one another.

The first connection portion 20' provides an input port 22 of the actuation winding 20, and the second connection portion 21' provides an output port 23 of the detection winding 21.

The actuation loop 20" traverses the main portion 17 along its perimeter, parallel to the sides of the main portion 17. Likewise, also the detection loops 21" traverse the main portion 17 along its perimeter and can be partially superimposed on the actuation loop 20" but not in direct electrical contact therewith.

A pair of magnets 25 (or, alternatively, a single permanent magnet) are set in the proximity of the microbalance 10, on opposite sides thereof, so as to generate a magnetic field B having field lines with direction perpendicular to the axis of symmetry 15 passing through the first and second arms 12, 13. The magnets 25 can be, for example, permanent magnets made of neodymium-iron-boron (NdFeB), having dimensions smaller than 1 mm$^3$, which are able to generate a magnetic field of approximately 0.1 T.

If on the input port 22 of the actuation winding 20 an input voltage $V_{in}$ is applied to generate a current $I_{in}$ through the actuation winding 20, on the sides of the microbalance 10 orthogonal to the field lines of the magnetic field B, as is known, the Lorentz force F is exerted, given by $$F = l \cdot I_{in} \cdot i \wedge B \tag{1}$$

where l is the length of the portion of the actuation winding 20 that lies on the side on which the Lorentz force F is exerted, and i is a unit vector with a direction parallel to the portion of the actuation winding 20 on which the Lorentz force F is exerted and the same sense as the current $I_{in}$.

The Lorentz force F is, instead, zero on the sides of the microbalance 10 parallel to the field lines of the magnetic field B.

There is hence generated on the microbalance 10 a twisting moment τ, which induces a rotation of the mobile body 11 about the axis of symmetry 15

$$\tau = \sum_i F_i \wedge b_i \tag{2}$$

where $F_i$ is the force that acts on the i-th loop of the actuation winding 20, and $b_i$ is the arm of the moment that acts on the i-th loop of the actuation winding 20.

From Eqs. (1) and (2) we find that the magnitude $\tau_m$ of the twisting moment τ is given by $$\tau_m = 2blIB = A_{in}/B, \tag{3}$$

where $A_{in}$ is the area subtended by the actuation winding 20, and B is the magnitude of the magnetic field B.

In the specific example of FIG. 2, the actuation winding 20 comprises a single loop, and consequently the twisting moment τ is only due to the Lorentz force F that acts on opposite sides of the single loop of the actuation winding 20.

From Eq. (3) it may be assumed that the mobile body 11 of the microbalance 10 oscillates with a frequency of oscillation proportional to the frequency of the current $I_{in}$. During the oscillations of the mobile body 11, the first and second arms 12, 13 have the function of torsional springs. If the frequency of the current $I_{in}$ corresponds to the resonance frequency of the microbalance 10, the amplitude of the oscillations is a maximum.

The oscillations of the mobile body 11 are detected, in the presence of the magnetic field B, by the detection winding 21. As is known, according to the Faraday-Lance law, the oscillation of the mobile body 11 in the presence of the magnetic field B causes an increase in the flux of the field through the loops of the detection winding 21, generating an electromotive force that opposes the variation of flux across the detection winding 21 (output port 23). If the mobile body 11 rotates rigidly about the axis of symmetry 15, the output voltage $V_{out}$ on the output port 23 is given by $$V_{out} = -\frac{\partial \Phi_B}{\partial t} = A_{out} B \frac{\partial \sin\theta}{\partial t} \quad (4)$$

where $\Phi_B$ is the flux of external magnetic field B, $A_{out}$ is the area subtended by the detection winding 21, and θ is the angle of rotation of the mobile body 11. If the angle θ of rotation of the mobile body 11 is sufficiently small, Eq. (4) can be approximated as follows:

$$V_{out} \approx A_{out} B \frac{\partial \theta}{\partial t} \quad (5)$$

A possible application of the control system 1 regards the detection of complex organic molecules such as DNA or proteins. In this application, the use of the control system 1 provides a series of advantages as compared to commonly used optical-reading methods, based, for example, upon fluorescence techniques. In the first place, since no cumbersome optical detectors are required, it is possible to provide a totally integrated control system 1. In the second place, reading is extremely simple and affords an improved sensitivity, enabling detection of the presence of particular molecules and supply of a measurement of the weight, and hence of the amount, of said molecules. Finally, it is not necessary to pretreat the DNA or the proteins with an optical label.

However, since the mass of the molecules or of the compounds to be detected is normally extremely small, the sensitivity of MEMS microbalances of the type described generally proves insufficient for detecting concentrations of molecules below a certain minimum-amount threshold.

BRIEF SUMMARY

The present disclosure is directed to an integrated torsional-microbalance device obtained with MEMS technology, and a corresponding fabrication process. A MEMS microbalance is provided that includes a substrate made of semiconductor material having a cavity and a resonator suspended above the cavity of the substrate. The microbalance also includes a mobile body, at least a first arm, connected between the substrate and the mobile body, having a first thickness and designed to enable oscillations of the mobile body with respect to the substrate, an actuation transducer connected to the mobile body and designed to generate said oscillations at a resonance frequency, and a detection transducer designed to detect a variation in the resonance frequency, wherein the mobile body comprises at least a thin portion having a second thickness smaller than said first thickness of the first arm.

BRIEF DESCRIPTION OF THE SEVERAL VIEWS OF THE DRAWINGS

For a better understanding of the present disclosure, preferred embodiments are now described, purely by way of non-limiting example, with reference to the attached drawings, wherein:

FIGS. 5-11 show a cross-sectional view during successive fabrication steps of the microbalance of FIG. 4;

DETAILED DESCRIPTION

Figure 1:
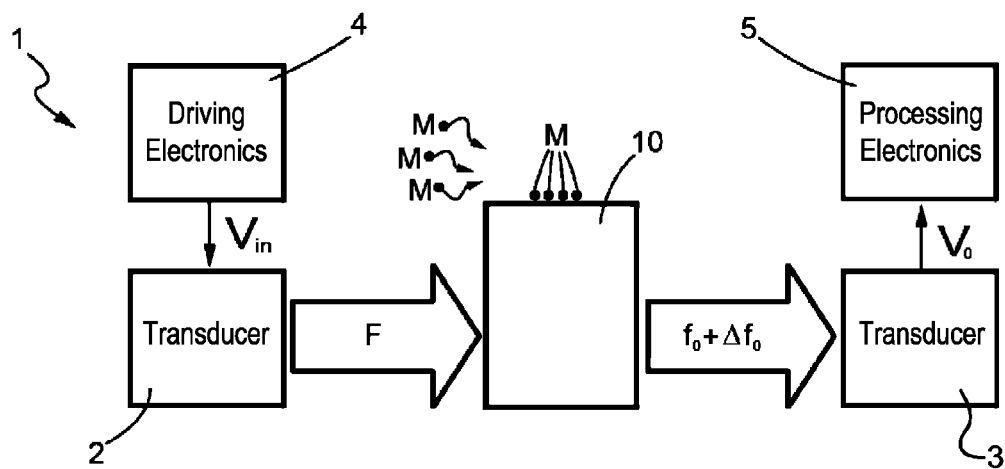
FIG. 1 is a schematic illustration of a control system of a known type, used for actuating a microbalance.
Figure 2:
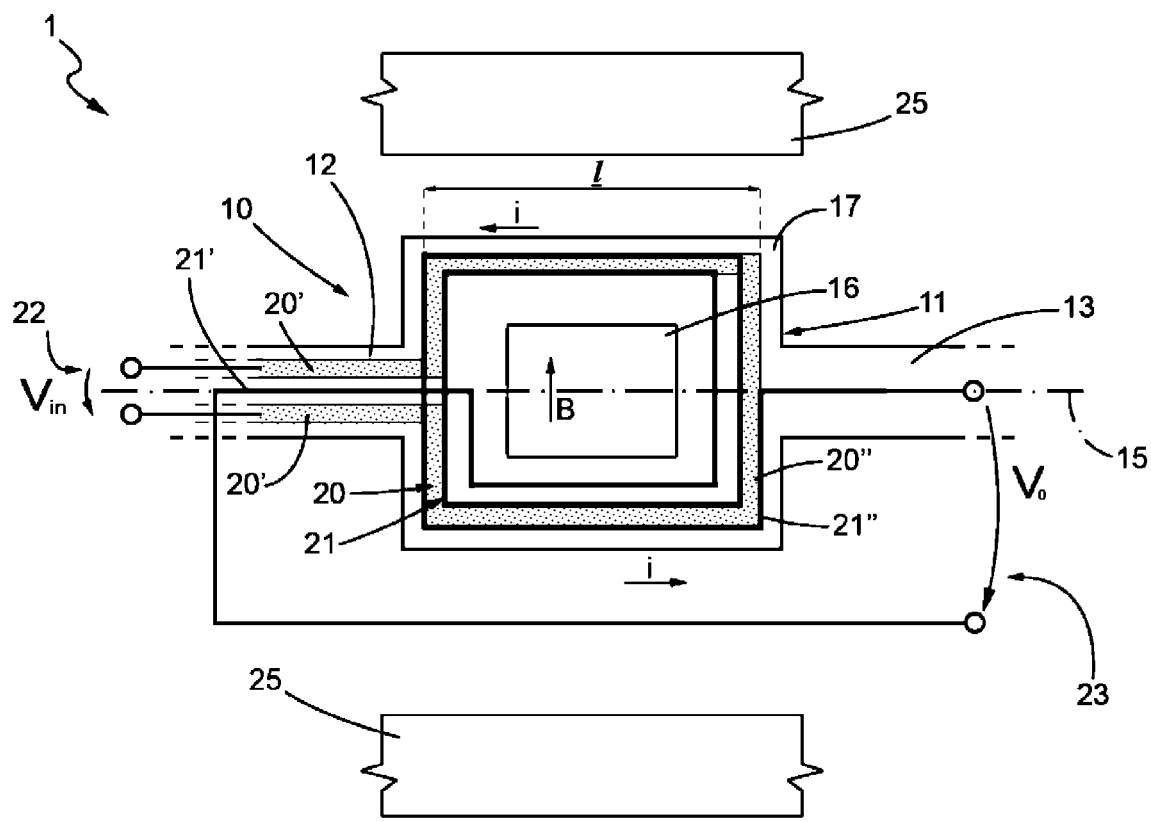
FIG. 2 shows a top plan view of an embodiment of a known type of the microbalance and of a corresponding control system of FIG. 1.
Figure 3:
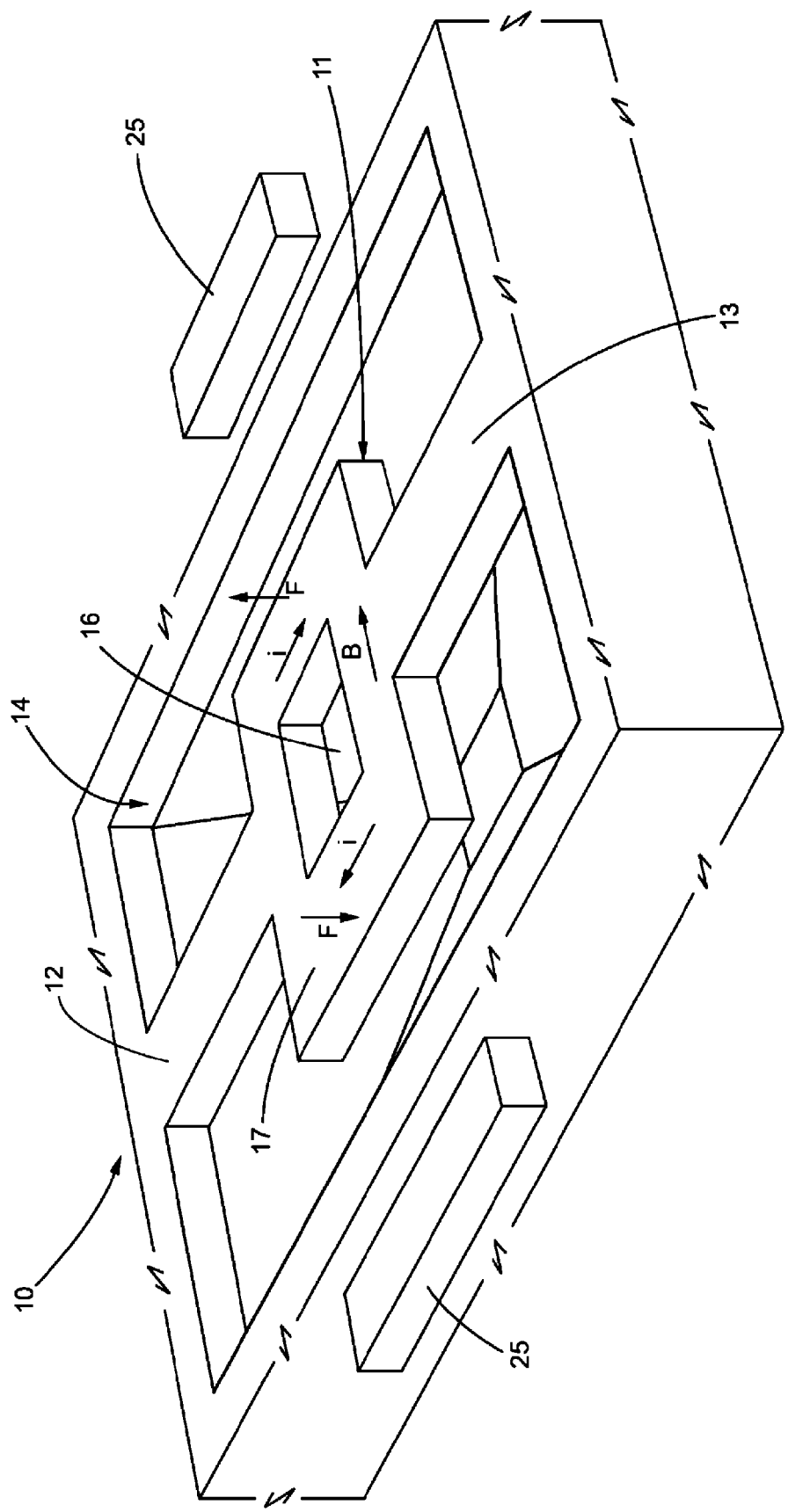
FIG. 3 shows a perspective view of the microbalance of FIGS. 1 and 2.
Figure 4:
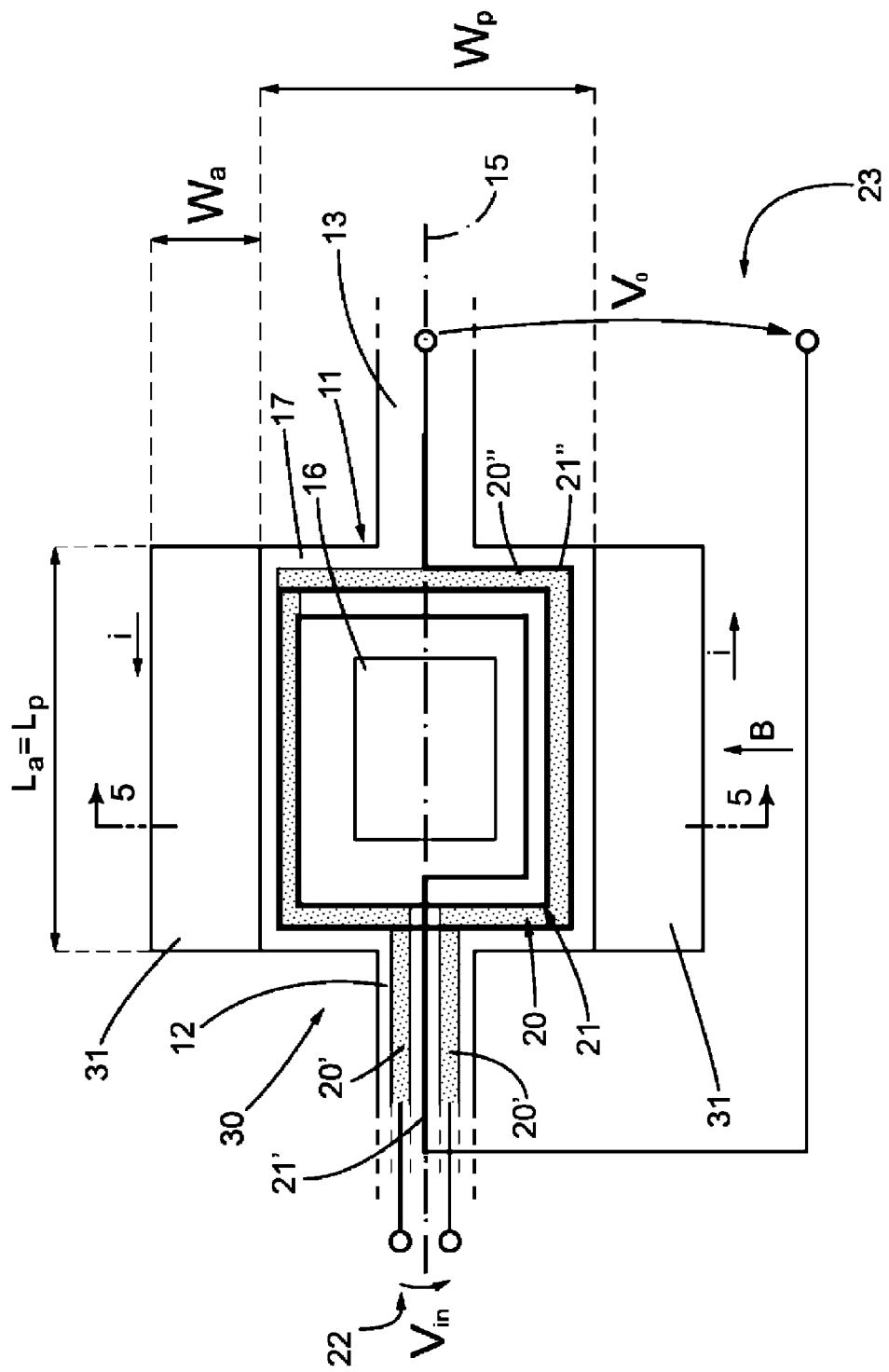
FIG. 4 shows a top plan view of a microbalance according to one embodiment of the present disclosure.
Figure 10:
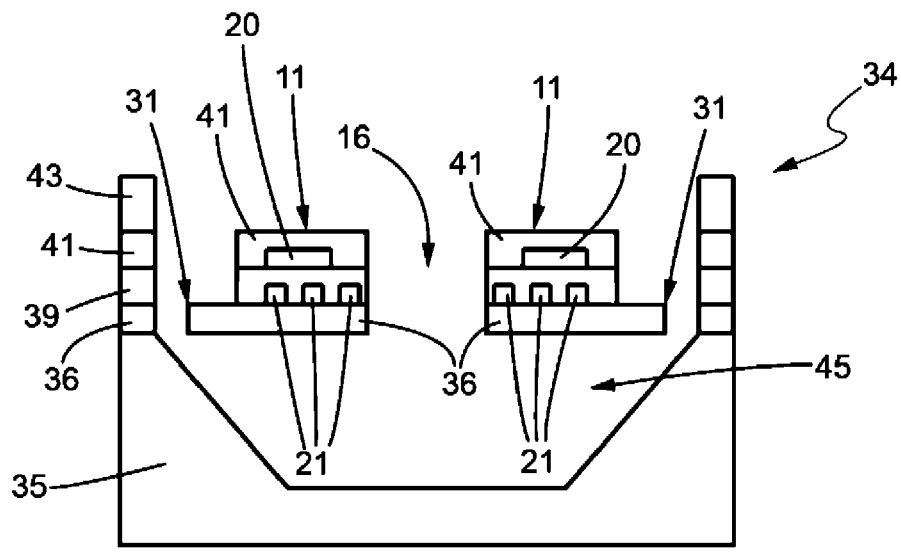

FIG. 4 shows a microbalance 30 with increased sensitivity, according to one embodiment. Elements of the microbalance 30 of FIG. 4 that are common with those of the microbalance 10 of FIG. 2 are here designated by the same reference numbers, and are not further described.

As compared to microbalances of a known type (for example, the microbalance 10 of FIG. 2), the microbalance 30 of FIG. 4 further comprises appendages 31 (also referred to as "wings"), arranged on opposite sides of the main portion 17 and fixed with respect thereto. In greater detail, the appendages 31 extend as a prolongation of the main portion 17 externally with respect to the actuation and detection windings 20, 21, and are fixed with respect to the sides on which the Lorentz force F acts.

For example, the main portion 17 of the microbalance 30 can have a rectangular shape, with sides parallel to the axis of symmetry 15 having a length $L_p$ comprised between 50 μm and 500 μm, for example, 200 μm, sides perpendicular to the axis of symmetry 15 having a length $W_p$ comprised between 50 μm and 500 μm, for example, 400 μm, and a thickness $H_p$ comprised between 3 μm and 6 μm, for example, 4.8 μm. The appendages 31 can have a rectangular shape with sides parallel to the axis of symmetry 15 of a length $L_a$ coinciding with the length of the side of the main portion 17 with respect to which they are fixed, for example, $L_a=L_p=200$ μm, and a length of the remaining sides of, for example, $W_a=(\frac{1}{3})L_a=66$ μm and a thickness $H_a=(\frac{1}{4})H_p=1.2$ μm.

A preferred application of the microbalance 30 regards detection and/or measurement of the mass and of the weight of molecules deposited on the microbalance 30, and in particular on just the appendages 31.

Alternatively, the microbalance 30 can be used for dynamic measurement, in situ, of the thickness reached by a layer of material during a deposition process, for example of a sputtering type or by evaporation.

For detection and/or measurement of masses of molecules or portions of organic molecules (for example, DNA, proteins, etc.) and inorganic molecules (for example, CO, $NO_2$, etc.), the surface of the mobile body 11 and/or of the appendages 31 must be appropriately treated, for example, by depositing a bond layer designed to favor chemical and non-chemical bonds with molecules or portions of molecules so as to be able to withhold only the molecules of interest.

For detection of specific DNA sequences ("target" sequences), it is instead expedient to favor grafting, on the mobile body 11 and/or on the appendages 31, of DNA sequences ("probe" sequences) complementary to the target sequences, and hence enable hybridization of the target sequences with the probe sequences.

For detection of specific proteins, it is instead possible to functionalize the surface of the mobile body 11 and/or of the appendages 31 by means of appropriate antibodies designed to bind with the proteins to be detected, or, alternatively, it is possible to form chemically active self-assembled monolayers (SAMs), designed to form an electrostatic or covalent bond with the proteins of interest.

For detection of inorganic molecules, the bond layer is, for example, constituted by a polymer capable of absorbing the molecules of interest selectively. For detection, for example, of octane, toluene, and other hydrocarbons, it is possible to use polymers such as polyether urethane (PEUT), polyacryl amide (PAAM), polyethylene glycols (PEG), poly 4-styrene-sulphonate (PSS), polyvinyl alcohol (PVA), and others still.

In use, the microbalance 30 is conveniently actuated at a resonance frequency $f_0$ of its own. For example, the microbalance 30 can be inserted in an oscillator reaction loop (not shown) in such a way that the output signal $V_o$ will be fed back, possibly amplified, on the input port 22 (driving signal $V_{in}$) so as to maintain an oscillation at the resonance frequency $f_0$.

The hybridization of the target sequences with the probe sequences or the retention by the bond layer or SAM of a sufficient amount of inorganic or organic molecules causes an increase of the mass (and of the weight) of the microbalance 30, and consequently generates a variation of the resonance frequency $f_0$.

The percentage variation of the resonance frequency $f_0$ is indicative of the sensitivity of a microbalance. Thus, given a certain additional mass on the microbalance 30 of molecules, portions of molecules, or other deposited material, the greater the sensitivity of the microbalance 30, the higher the ratio between the total additional mass and the mass of the microbalance 30 at rest (i.e., without additional mass). In planar structures (i.e., ones having a thickness that is much smaller than the width and the length of the structure itself), the sensitivity is inversely proportional to the thickness of the microbalance 30. The thickness of the microbalance 30, and in general of the majority of similar resonant mechanical structures, cannot, however, be reduced below a minimum value necessary for integrating, in the microbalance 30, structural elements and/or the actuation and detection windings 20, 21.

Instead, since the appendages 31 are external to the actuation and detection windings 20, 21, they can be as thin as desired, within the limits of minimum thickness dictated by mechanical solidity and the technological process employed. Consequently, in points corresponding to the appendages 31, the ratio between the density of additional total mass per unit surface and the density of mass per unit surface of the appendages 31 is maximum.

The inertia of the appendages 31 prevails over the inertia of the main portion 17 and hence their reduced mass density per unit surface proves to have a beneficial effect on sensitivity. In fact, the moment of inertia of the main portion 17, calculated for a rotation of the main portion 17 about the axis of symmetry 15, is dominated by the moment of inertia of the appendages 31 in so far as the mass per unit surface is mathematically weighted by the square of its distance from the axis of symmetry 15. Consequently, regions of the main portion 17 and of the appendages 31 that are more distant from the axis of symmetry 15 have a mathematical weight that is greater than regions close to the axis of symmetry 15.

The resonance frequency $f_0$ of the microbalance 30 is markedly affected by the moment of inertia introduced by the appendages 31, and hence, in the presence of an additional mass on the appendages 31, the resonance frequency undergoes a percentage variation that is greater as compared to embodiments of a known type without appendages 31.

This leads to a considerable advantage in terms of sensitivity of the microbalance 30. For example, with reference to FIG. 4, if rectangular appendages 31 are formed having dimensions $L_a=L_p$, $W_a=(\frac{1}{3})W_p$, and $H_a=(\frac{1}{4})H_p$, a value of sensitivity is obtained increased by approximately two and a half times with respect to the value of sensitivity of microbalances 10 of a known type.

To obtain an increase in sensitivity that is three times as much, it is convenient instead to achieve a ratio $W_a=(\frac{1}{2})W_p$, whilst the length of the sides of the opening 16 is in this case half the length of the sides of the main portion 17 that they face. In any case, with an opening 16 having the above dimensions or smaller ones, the increase in sensitivity is independent both of the dimensions of the opening 16 itself and of the length $L_p$ of the main portion 17. It is moreover expedient to specify that the data of increase in sensitivity indicated previously are obtained considering the entire surface of the microbalance 30 (hence the surface of the appendages 31 and the surface of the main portion 17) coated by the bond layer.

FIGS. 5-10 show a cross section of the microbalance 30 along a line of cross section V-V of FIG. 4, during successive fabrication steps for providing the microbalance 30.

A wafer 34, comprising a silicon substrate 35, is subjected to standard "front end" steps.

Initially (FIG. 5), a bearing layer 36 is deposited, for example, made of field oxide (FOX) and/or pre-metal dielectric (PMD) with a thickness of 1.2 μm, having a function of defining a resting base on which the actuation and detection windings 20 and 21 are provided.

Then (FIG. 6), a first metal layer, for example aluminum, is deposited to form the first metal level and defined so as to provide the detection winding 21 and first mask regions 37, having, as illustrated better hereinafter, a function of defining the shape of the appendages 31. Preferably, the detection winding 21 is formed by a metal line that is wound above the bearing layer 36 to form the plurality of concentric detection loops 21" (the two loops in the example shown in FIG. 4) and the second connection portion 21' set on the second arm 13.

A first intermetal layer 39, made of dielectric material, is deposited on the wafer 34 for protecting and insulating the first mask regions 37 and the detection winding 21, and is finally planarized.

Next (FIG. 7), on the first intermetal layer 39 a second metal layer, for example aluminum, is deposited to form the second metal level and defined to provide the actuation winding 20 and the second connection portion 21' set on the first arm 12.

The actuation winding 20 comprises the actuation loop 20" (a single loop in the example shown in FIG. 4) and the first connection portion 20', set on the first arm 12. In this case, the actuation loop 20" has a width greater than that of a single detection loop 2r.

A second intermetal layer 41, made of dielectric material and more in particular of the same material used for the first intermetal layer 39, is deposited on the wafer 34 to protect and insulate the actuation winding 20 during the subsequent fabrication steps. The second intermetal layer 41 is then planarized.

Alternatively, with joint reference to FIGS. 4 and 7, the connection portion 21' of the detection winding 21 set on the first arm 12 and having the function of connection between the detection winding 21 and the output port 23, can be obtained in a metal level different from the one in which the detection loops 21" are provided. For example, as described, they can be made in the same metal level (second metal level) of the actuation winding 20 to prevent creation of a transverse electrical contact between concentric detection loops 21".

For this purpose, in a way not shown in the figure, a connection contact (a pad) can be provided between the detection loops 21" made in the first metal level and the connection portion 21' made in the second metal level.

Next (FIG. 8), on the second intermetal layer 41 a third metal layer, for example aluminum, is deposited to form a third metal level and defined to provide second mask regions 42.

The second mask regions 42 have the function, as will be better illustrated hereinafter, of defining the shape of the mobile body 11 and of the first and second arms 12, 13.

Then, a passivation layer 43 (for example, nitride) is grown on the wafer 34, on the second intermetal layer 41 and the second mask regions 42. The passivation layer 43 has a function of protection, during fabrication, of the driving and processing electronics (not illustrated) when said electronics are provided in an integrated way on one and the same chip of the microbalance 30, simultaneously with the steps of fabrication of the microbalance 30.

Next, the passivation layer 43 is selectively removed from the wafer 34 so as to leave the second mask regions 42 and portions of the second intermetal layer 41 exposed. A subsequent etching step (FIG. 9), for example, wet etching, carried out for 30 min using a buffered-hydrofluoric-acid (BHF) solution, enables selective removal of the second intermetal layer 41, the first intermetal layer 39, and the bearing layer 36 in regions of the wafer 34 not protected by the passivation layer 43, by the first mask regions 37, and by the second mask regions 42. The isotropic nature of wet etching with BHF, having an excessive lateral removal (in a direction parallel to the substrate 35) of the first and second intermetal layers 39, 41 can lead to partial exposure of the actuation winding 20 and/or of the detection winding 21. This should be avoided in so far as successive fabrication steps could cause damage to the areas of the actuation and detection windings 20 and 21, respectively, if exposed. To overcome this problem, it is advisable to set the actuation and detection windings 20 and 21 at a distance of at least 10 μm from external sides provided for the main portion 17 and form the sides internal to the main portion 17, envisaged for delimiting the opening 16. For this purpose, the second mask regions 42 are provided on and aligned with the actuation and detection windings 20, 21, and extend alongside the actuation winding 20 and/or the detection winding 21 for a length of at least 10 μm.

Alternatively, it is possible to use an etch of an anisotropic type, for example, deep reactive ion etching (DRIE), thus rendering the precautions of minimum lateral distance envisaged for the actuation and detection windings 20 and 21, respectively, less stringent.

During the step of wet etching with BHF, the first mask regions 37 protect the underlying portion of bearing layer 36, preventing removal and thus defining the shape of the appendages 31, which are obtained as prolongations of the bearing layer 36 and possess the characteristics thereof of thickness, stiffness, and mass density, for example. Likewise, the second mask regions 42 define the shape of the mobile body 11 and of the opening 16.

Finally (FIG. 10), the first and second mask regions 37, 42 are removed, for example, by means of wet etching using a solution of 71.6% $H_3PO_4$, 3.4% $CH_3COOH$, and 25% deionized water, for a approximately 10 min at a temperature of 40° C. so as to expose the mobile body 11 and the appendages 31.

The opening 16 is used to facilitate removal, for example, by means of wet etching with tetramethyl ammonium hydroxide (TMAH) for approximately 165 min at a temperature of 80° C., of the substrate 35 underneath the main portion 17 and of the first and second arms 12, 13 of the microbalance 30, providing a structure suspended above a cavity 45.

Figure 11:
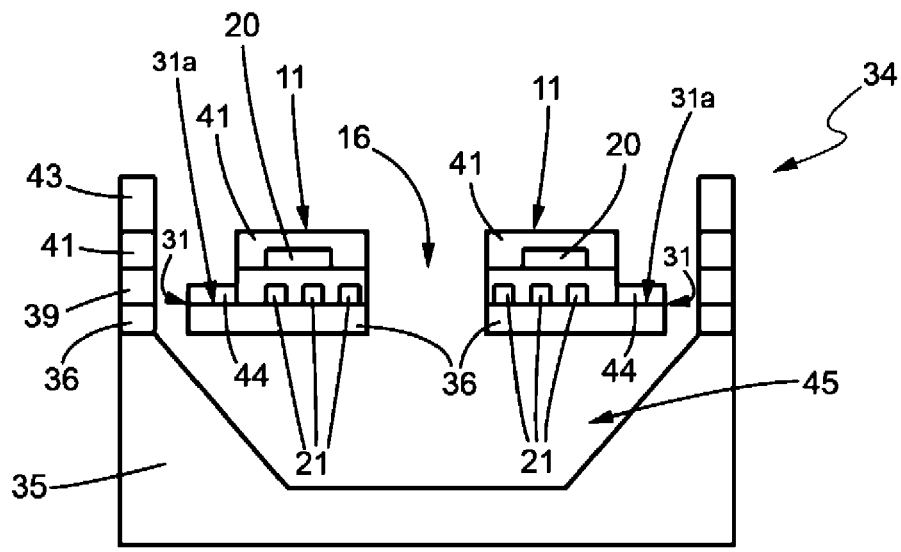

FIG. 11 shows a subsequent step of deposition and definition of a bond layer 44, for example, a polymeric layer (PEUT, PAAM, PEG, PMMA, etc.), on a top surface 31a of the appendages 31 (alternatively, in a way not shown in the figure, it is possible to deposit the bond layer 44, not only on a top surface 31a of the appendages 31, but also on the entire surface of the main portion 17).

This deposition step can alternatively be replaced by a functionalization step (not shown) of the top surface 31a of the appendages 31 with probe sequences of DNA or antibodies.

According to a further embodiment (shown in FIG. 12), it is possible to increase further the sensitivity of the microbalance 30 by providing the actuation loop 20" and the detection loops 21" on one and the same metal level, thus reducing the thickness of the main portion 17.

Figure 12:
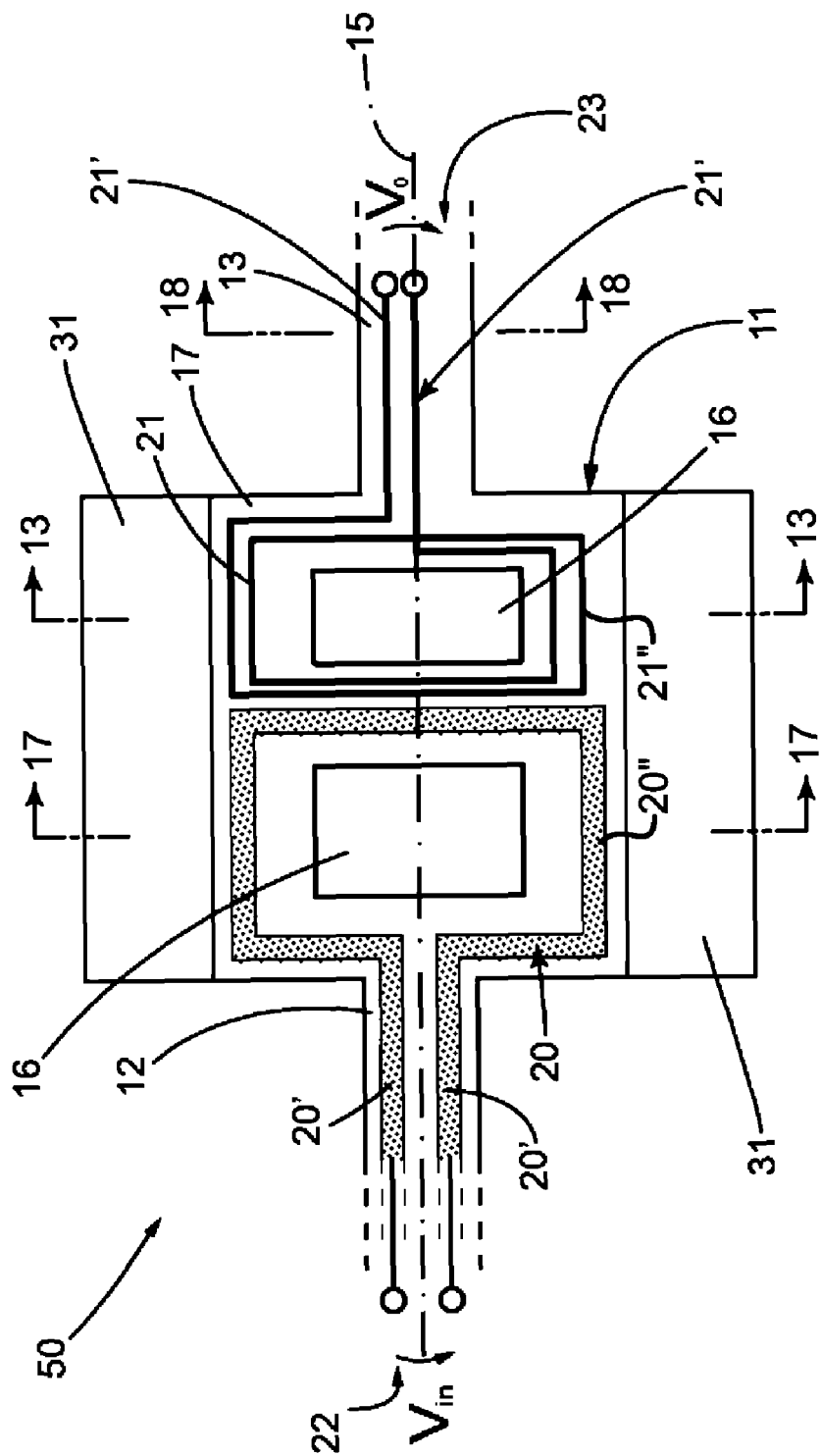
FIG. 12 shows a top plan view of a microbalance according to a further embodiment of the present disclosure.
Figure 13:
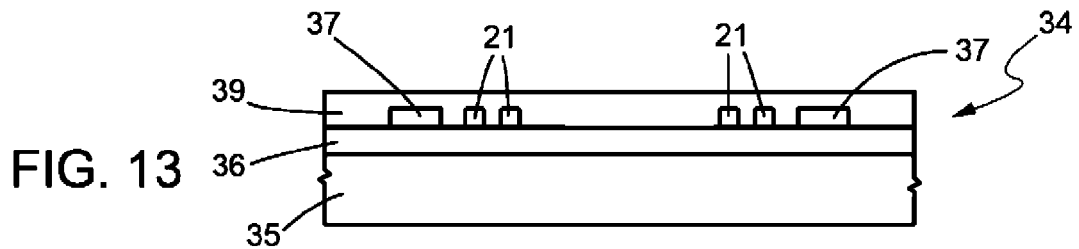
FIGS. 13-16 show a cross-sectional view along a line of cross section XIII-XIII during successive fabrication steps of the microbalance of FIG. 12.
Figure 14:
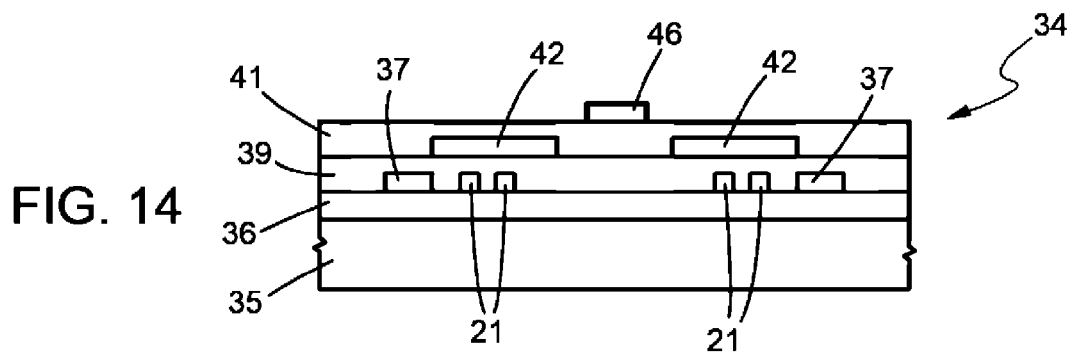
Figure 15:
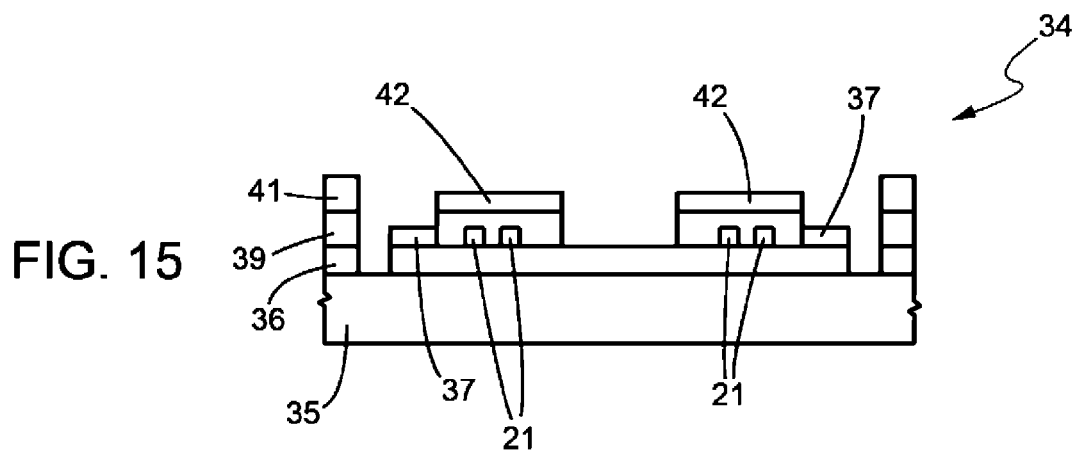
Figure 16:
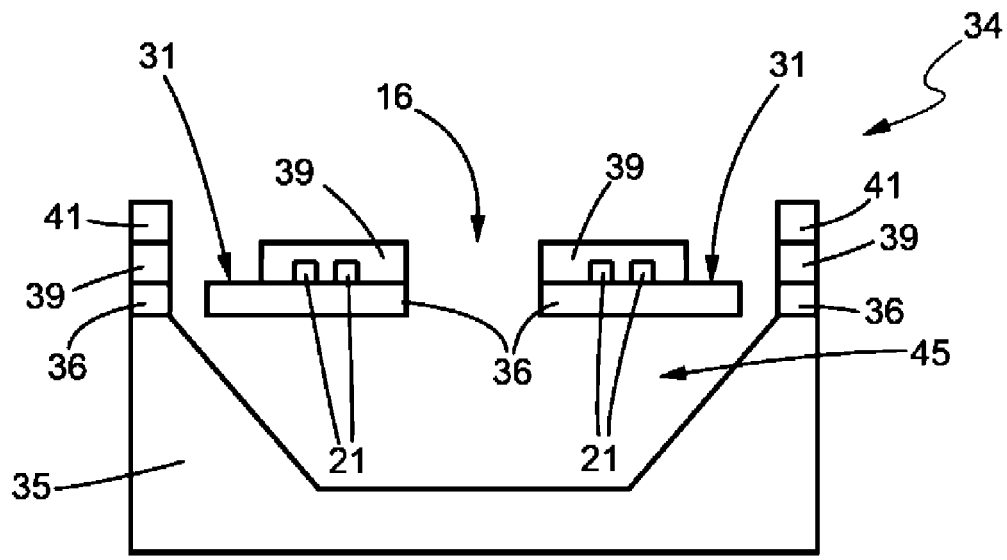

FIG. 12 shows a top plan view of a microbalance 50 according to said further embodiment. Elements that are similar to those of the microbalance 10 of FIG. 2 and to those of the microbalance 30 of FIG. 4 are not described further and are designated in FIG. 12 by the same reference numbers.

Since the actuation loop 20" and the detection loops 21" are obtained on one and the same metal level, the actuation loop 20" and the detection loops 21" are not superimposed on one another, but are set alongside one another. Consequently, the first connection portion 20' of the actuation winding 20 is set entirely on the first arm 12, whilst the second connection portion 21' of the detection winding 21 is set entirely on the second arm 13 of the microbalance 50. In addition, in this case, two openings 16 are present, each made inside the respective actuation winding 20 and detection winding 21.

To prevent creation of a direct electrical contact between the concentric loops of the actuation winding 21, also in this case it is expedient to form the second connection portion 21' on two different metal levels. In this way, only the second arm 13 possesses a large thickness due to the presence of two metal levels, in a way similar to the microbalance 30 of FIG.

4, whilst the main portion 17 is thinner (and in particular it comprises one metal level less).

For structural uniformity, it may be convenient to made the first arm 12 with the same thickness as the second arm 13. In this way, there is a reduction in the possible disadvantages such as the increase of the resonance modes of the structure (lower spectral purity of the oscillation produced inserting the microbalance 50 in a reaction loop of an oscillator), or else the lower mechanical solidity that could be the cause of failure of the arm of smaller thickness.

The steps of fabrication of the microbalance 50 are described with reference to FIGS. 13-16, which show a cross-sectional view along a line of cross section XIII-XIII of FIG. 12, to FIG. 17, which shows a cross-sectional view along a line of cross section XVII-XVII of FIG. 12, and to FIG. 18, which shows a cross-sectional view along a line of cross section XVIII-XVIII of FIG. 12.

In the first place (FIG. 13), the substrate 35 is provided, and the bearing layer 36 is deposited on the substrate 35 (in a way similar to what has been described with reference to FIG. 5). Then, a first metal layer, for example aluminum, is deposited to form the first metal level, and is then defined so as to provide the detection winding 21, the actuation winding 20, and the first mask regions 37.

Next, the first intermetal layer 39, made of dielectric material, is deposited to protect and insulate the first mask regions 37, the actuation winding 20, and the detection winding 21.

Figure 18:
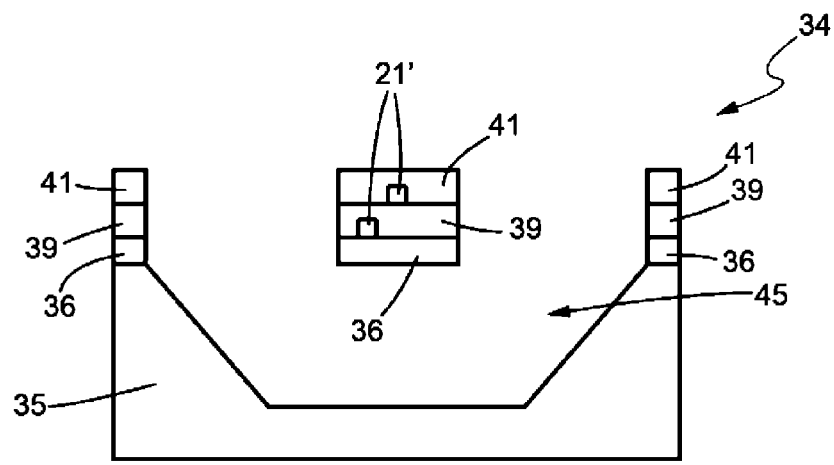

Then (FIG. 14), on the first intermetal layer 39, a second metal layer, for example aluminum, is deposited to form a second metal level, and is defined to provide the second mask regions 42 and the connection portion 21' of the detection winding 21 that develops on the second metal level (the connection portion 21' formed on two metal levels is shown in cross section in FIG. 18). In this step, the second mask regions 42 define exclusively the shape of the main portion 17 and not that of the first and second arms 12, 13.

Next, on the mask regions 42 and on the connection portion 21', the second intermetal layer 41 is deposited. A subsequent deposition and definition of a third metal layer (third metal level), on the second intermetal layer 41, provides third mask regions 46 for defining the shape of the first and second arms 12, 13 (since the third mask regions 46 do not lie along the line of cross section XIII-XIII, they are shown for purposes of greater clarity in FIG. 14 but are not shown in the subsequent FIGS. 15-17).

A successive wet-etching step (FIG. 15) enables removal of the second intermetal layer 41, the first intermetal layer 39, and the bearing layer 36 in portions not protected by the first, second, and third mask regions 37, 42, 46.

Finally (FIG. 16), the first, second, and third mask regions 37, 42, 46 are removed, and the substrate 35 underneath the main portion 17 and the first and second arms 12, 13 of the microbalance 50 is etched, for example with TMAH, thus providing a structure suspended above the cavity 45.

Figure 17:
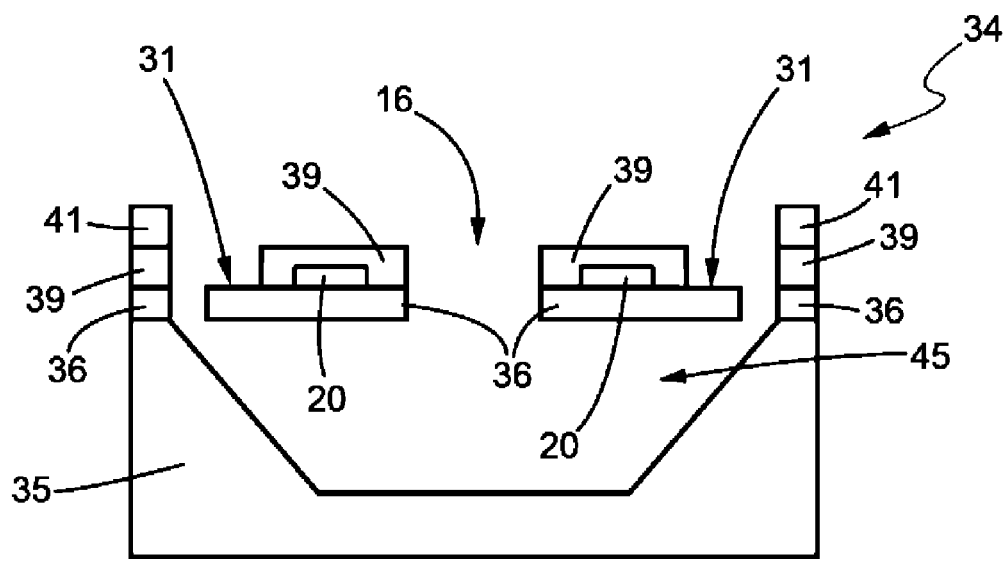
FIGS. 17 and 18 show a cross-sectional view respectively along a line of cross section XVII-XVII and a line of cross section XVIII-XVIII of the microbalance of FIG. 12 following upon the fabrication steps of FIGS. 13-16.

FIGS. 17 and 18 show a cross-sectional view of the microbalance 50 at the end of the process steps described with reference to FIGS. 13-16, along the respective lines of cross section XVII-XVII and XVIII-XVIII of FIG. 12.

It is possible to envisage, if need be, a subsequent step of deposition of a bond layer (not shown) on the appendages 31 and/or on the mobile body 11 or, alternatively, the functionalization of the surface of the appendages 31 and/or of the mobile body 11.

Figure 19:
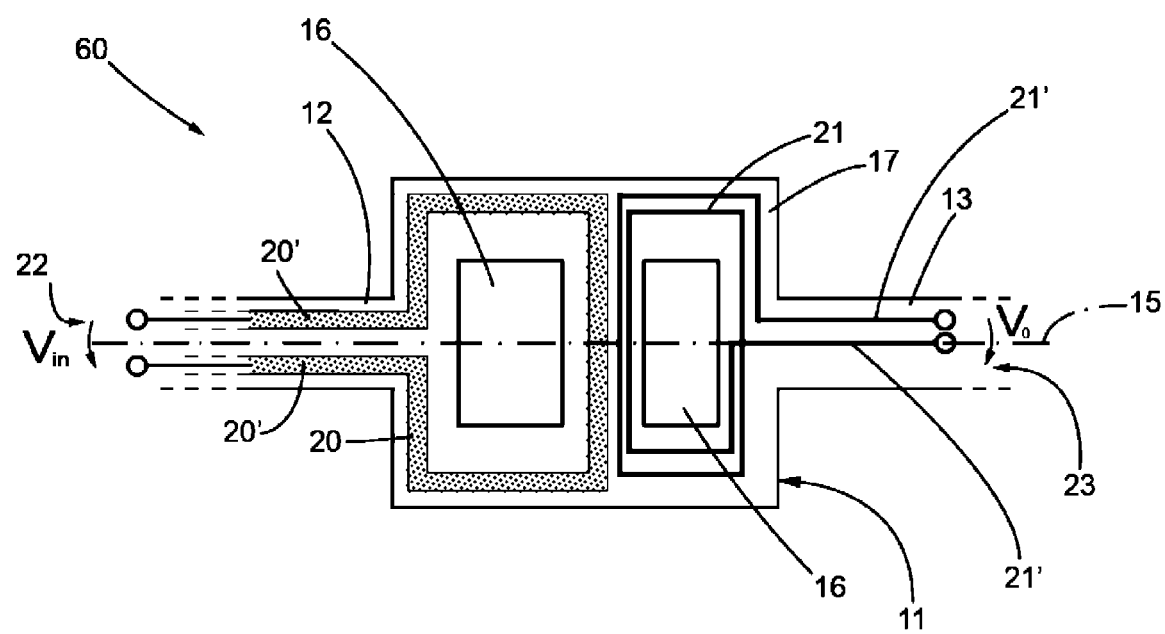
FIG. 19 shows a top plan view of a microbalance according to a further embodiment of the present disclosure.

FIG. 19 shows a microbalance 60 according to a further embodiment.

The microbalance 60 differs from the microbalance 50 of FIG. 12 in so far as it does not comprise the appendages 31.

The process of fabrication is similar to the one illustrated with reference to the microbalance 50, but does not comprise the step of formation of the appendages 31 (and hence of the first mask region 37). This embodiment is particularly advantageous in the case where it is intended to minimize the space occupied by the microbalance 60 and/or simplify the fabrication process maintaining in any case an increased sensitivity as compared to the microbalance 10 of FIG. 2.

Figure 20:
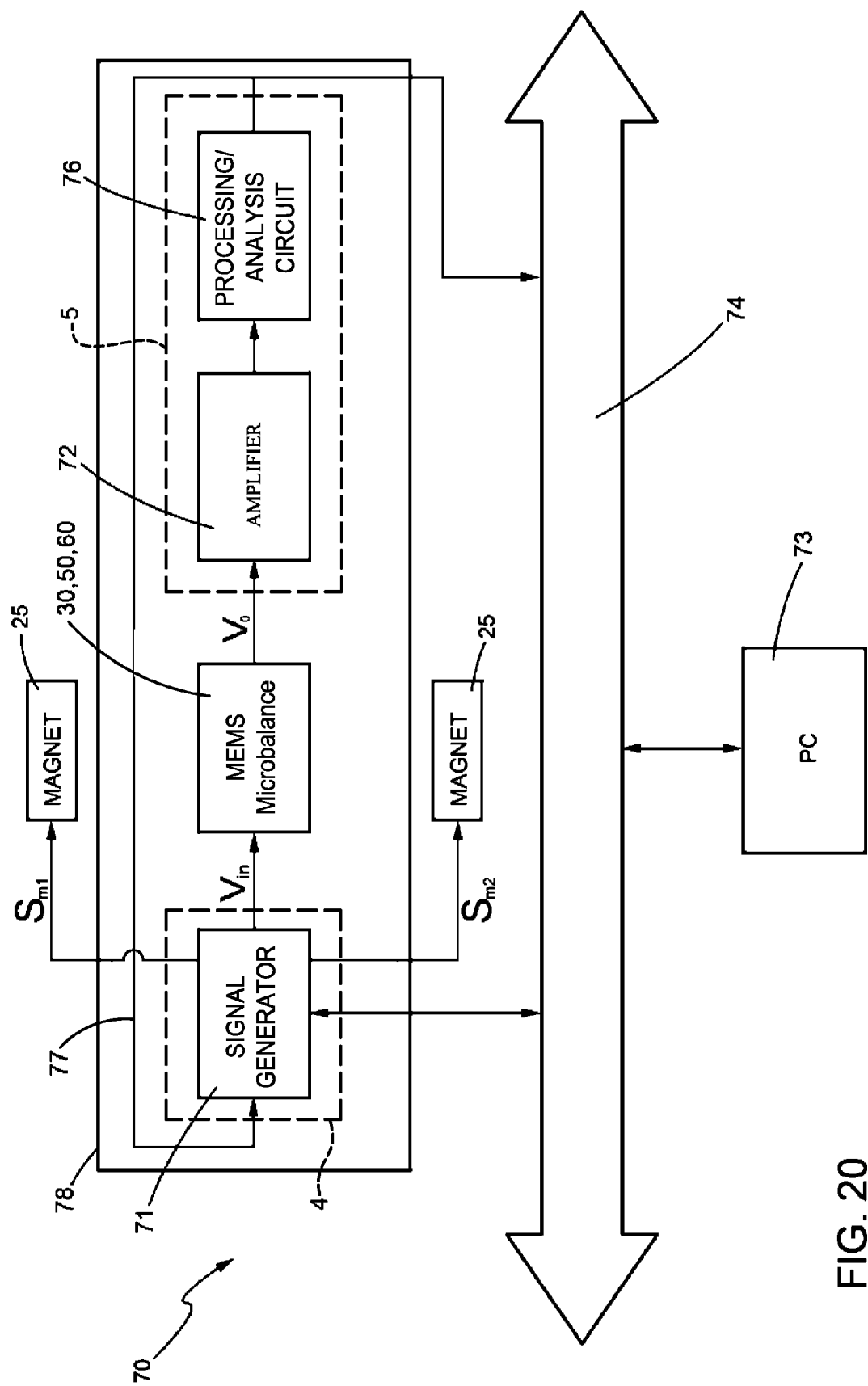
FIG. 20 shows a control and reading system of a microbalance according the present disclosure.

FIG. 20 shows an embodiment of a control and reading system 70 for the microbalance that may be one of the microbalances described herein, 30, 50 or 60. The system 70 includes the driving electronics 4, for example comprising: a signal generator 71, for generating the driving signal $V_{in}$ for actuation of the microbalance 30, 50 or 60 and possibly control signals $S_{m1}$, $S_{m2}$ to enable generation of the magnetic field by the magnets 25 (for example, the magnets 25 can be formed by electromagnets); the processing electronics 5, comprising an output amplifier 72 and a processing and/or analysis circuit 76; and, optionally, an oscillator reaction loop 77, for feeding the output signal $V_o$ on the input port 22 of the microbalance 30, 50, 60.

Advantageously, the driving electronics 4, the processing electronics 5, and the oscillator reaction loop 77 can be integrated in a single chip 78 together with the microbalance 30, 50, 60.

In addition, via a system bus 74, it is possible to connect the driving electronics 4 and the processing electronics 5 to a computer 73, having a function of aid to generation of the driving signal $V_{in}$ and aid to processing and analysis of the output signal $V_o$ for assessing a possible variation of the resonance frequency $f_0$.

The embodiments of the present disclosure described present numerous advantages. For example, as regards the microbalance 50 and the microbalance 60, shown respectively in FIGS. 12 and 19, and having the actuation and detection windings 20, 21 set alongside one another, the mutual inductance between the actuation winding 20 and the detection winding 21 is considerably reduced. The reduction in the mutual inductance moreover generates a reduction in the parasitic signal which would otherwise be superimposed on the useful signal, thus degrading it. In use, in fact, the parasitic signal must be much smaller than the useful signal generated when the microbalance is in resonance conditions.

In addition, by setting the actuation and detection windings 20, 21 alongside one another, it is possible to reduce the dimensions of the microbalance without deteriorating the performance. Considering a planar inductance, the mutual inductance is in fact, to a first approximation, less than proportional to a coupling factor (depending, amongst other things, upon the relative arrangement of the actuation and detection windings 20, 21) multiplied by the geometrical average of the areas occupied by the actuation and detection windings 20, 21 (i.e., the square root of their product), whilst the useful signal is proportional to the square of the area occupied by the detection winding 21. On the other hand, the useful signal is proportional to the product of the areas occupied by the actuation and detection windings 20, 21. Hence, for a certain minimum area of the mobile body 11 (and consequently a minimum area occupied by the actuation and detection windings 20, 21), the useful signal will be lower than the parasitic signal. By setting the actuation and detection windings 20, 21 alongside one another and not superimposed (according to the embodiments of the microbalances 50 and 60), it is possible to reduce considerably the coupling factor, and hence the area of the mobile body 11, maintaining an acceptable level of useful signal.

Figure 21:
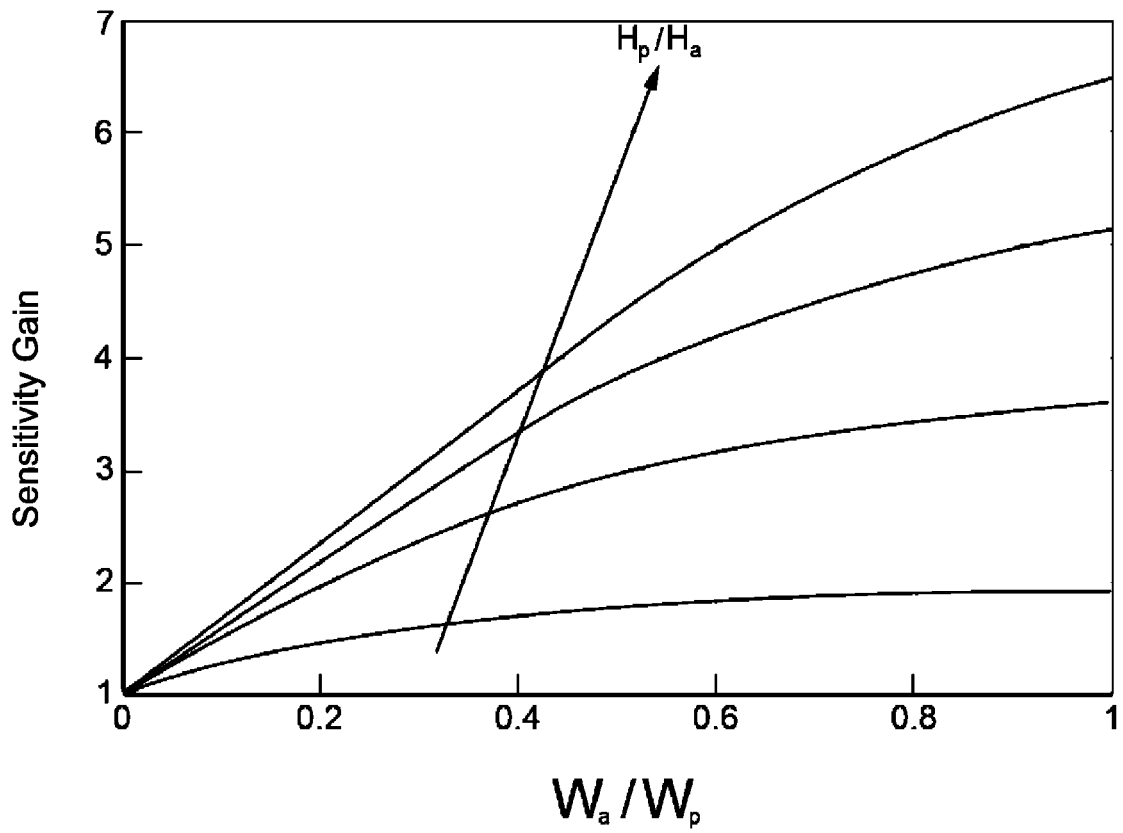
FIG. 21 shows sensitivity-gain curves as physical parameters of the microbalance provided with side appendages according to the present disclosure vary.

FIG. 21 shows sensitivity-gain curves as the ratio between the length $W_a$ of the side of the appendages 31 orthogonal to the axis of symmetry 15 and the length $W_p$ of the side of the main portion 17 orthogonal to the axis of symmetry 15 varies, for different ratios ranging between the thickness $H_p$ of the main portion 17 and the thickness $H_a$ of the appendages 31 (respectively, for values $H_p/H_a$ equal to 2, 4, 6 and 8).

The sensitivity curves are represented on a system of Cartesian axes in which the abscissa represents the ratio $W_a/W_p$, whilst the ordinate represents the sensitivity-gain value.

It may be noted that, by increasing the ratio $H_p/H_a$ (hence by reducing the thickness $H_a$ of the appendages 31), the sensitivity increases.

Finally, it is clear that modifications and variations can be made to the microbalance 30, 50, or 60 described and illustrated herein, without departing from the sphere of protection of the present disclosure.

For example, the actuation winding 20 and the detection winding 21 can comprise, independently, a greater number or a smaller number of loops, and can be obtained on metal levels different from the ones described. Since by reducing the dimensions of the actuation and detection windings 20 and 21 the useful signal deteriorates, it is possible to provide a plurality of actuation windings 20 and/or a plurality of detection windings 21 on different superimposed metal levels in order to increase the effectiveness of the actuation and/or detection.

Furthermore, it is possible to implement other types of actuation and detection, alternative to actuation and detection of a magnetic type.

For example, the actuation and detection transducers can be of a piezoelectric type. In this case, a layer of piezoelectric material may provide the actuation transducers, instead of providing in the microbalance the actuation and detection windings typical of actuation and detection of a magnetic type. The layer of piezoelectric material may be formed by deposition or implantation.

The detection transducers could moreover be made of a piezoresistive material. In this case during the fabrication steps deposition of a piezoresistive layer may be deposited.

Alternatively, the actuation and detection transducers can be of a thermal, thermomechanical, or capacitive type. In any case, it proves advantageous to introduce appendages 31 outside the area in which the actuation and detection transducers are formed.

Figure 22A:
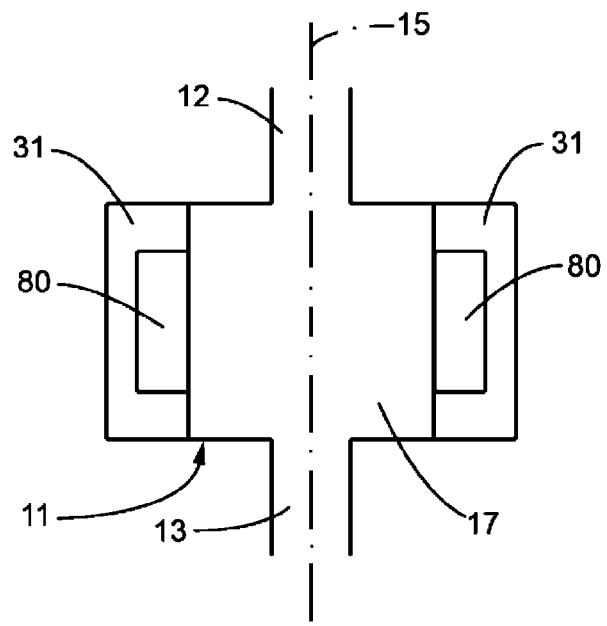
FIGS. 22a-22c show alternative embodiments of side appendages of a microbalance according to the present disclosure.
Figure 22B:
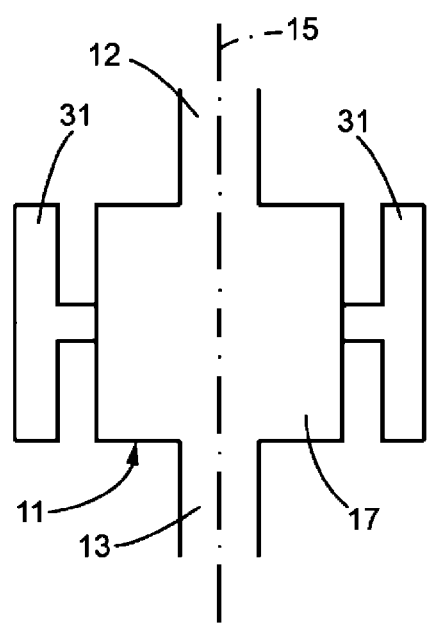
Figure 22C:
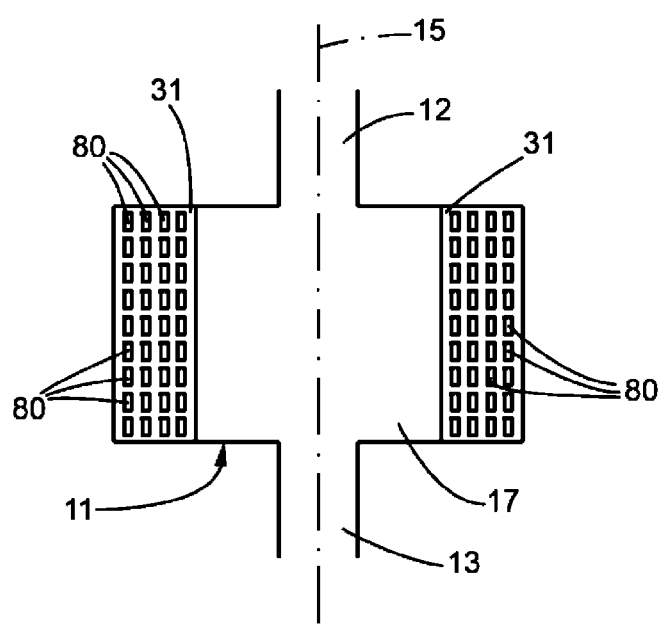

Finally, FIGS. 22a-22c show, in top plan view, alternative embodiments for the appendages 31. In FIGS. 22a-22c, the mobile body 11 and the first and second arms 12, 13 of the microbalance are schematically represented without the actuation and detection windings 20 and 21, in so far as it is possible to envisage appendages 31 for any type of microbalance, irrespective of the method of actuation and detection employed.

The shape of the appendages 31 can be optimized by introducing holes 80 or by shaping the appendages 31 so as to reduce damping due to the air, thus increasing a quality factor Q of the device. The quality factor Q is a measurement of the selectivity in frequency of the microbalance. The higher the value of the quality factor Q, the greater the attenuation of the components of the driving signal $V_{in}$ at frequencies different from the resonance frequency. Consequently, a high quality factor Q is indicative of a marked reduction of the noise introduced by the driving signal $V_{in}$, which can contain jitter and random variations of frequency. The noise could in fact cause variations of the frequency of oscillation that can be confused with the variations of frequency of oscillation due to the variation of mass of the device.

In conclusion, a high quality factor Q is indicative of the capacity to distinguish minimal variations of the resonance frequency and hence of a high resolution of the microbalance.

FIGS. 22a and 22c show two different embodiments of the appendages 31 comprising one (FIG. 22a) or more (FIG. 22c) holes 80 used for increasing the ratio between the surface and the volume of the appendages 31.

In this way, it is possible to obtain an increase in sensitivity according to the bond layer 44 used.

If, as an alternative to the bond layer 44, DNA probe sequences are used, also side walls of the holes 80 can be functionalized, thus increasing the density of reaction sites per unit surface and hence the likelihood of hybridization with target sequences.

If, instead, as bond layer 44, a polymer capable of capturing inorganic molecules is used, and if said polymer, after having been deposited, covers the holes 80, the perforated wing 31 coated with polymer proves in any case to have a mass density per unit surface lower than that of a wing 31 without holes 80, whilst the density of absorption sites per unit surface is the same, with consequent increase in sensitivity. In order to maximize the advantage, it is in any case advisable to use a polymer with mass density that is as low as possible as compared to the mass density of the material used for obtaining the appendages 31.

FIG. 22b shows a further embodiment of the appendages 31. In this case, the appendages 31 are without holes but are T-shaped.

It is clear that the appendages 31 can have any shape whatsoever, and can comprise any number of holes 80, which can also be of any shape.

Figure 23:
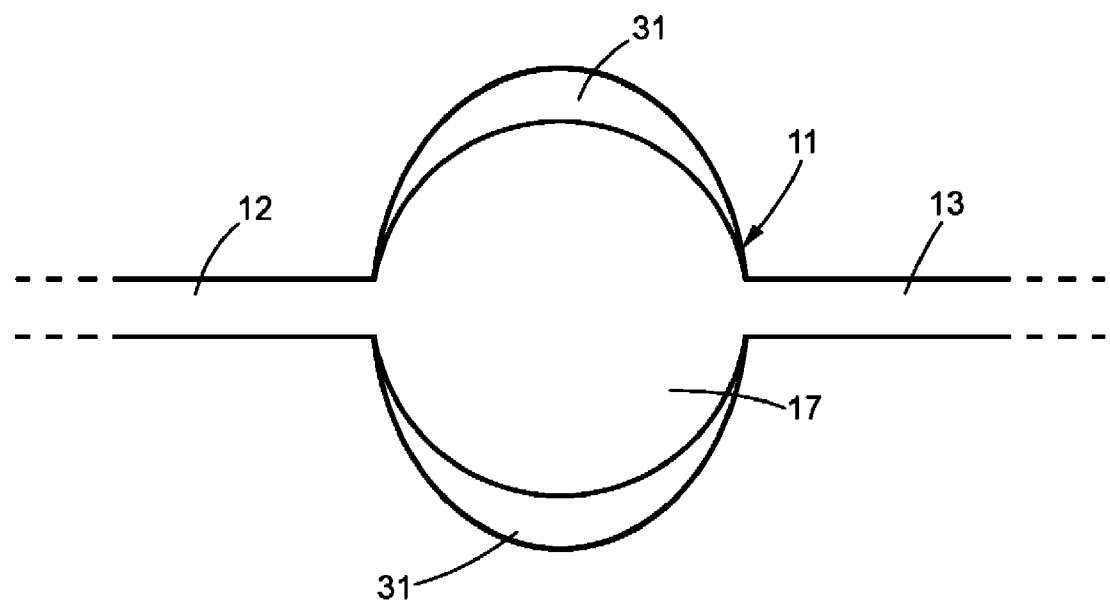
FIGS. 23 and 24 show alternative embodiments of a microbalance according to the present disclosure.

It is moreover clear that also the main portion 17 can be of any shape, even circular. In this case, the appendages 31 will have an appropriate shape, for example, be crescent-shaped or shaped like a circular segment, as is shown in FIG. 23.

Figure 24:
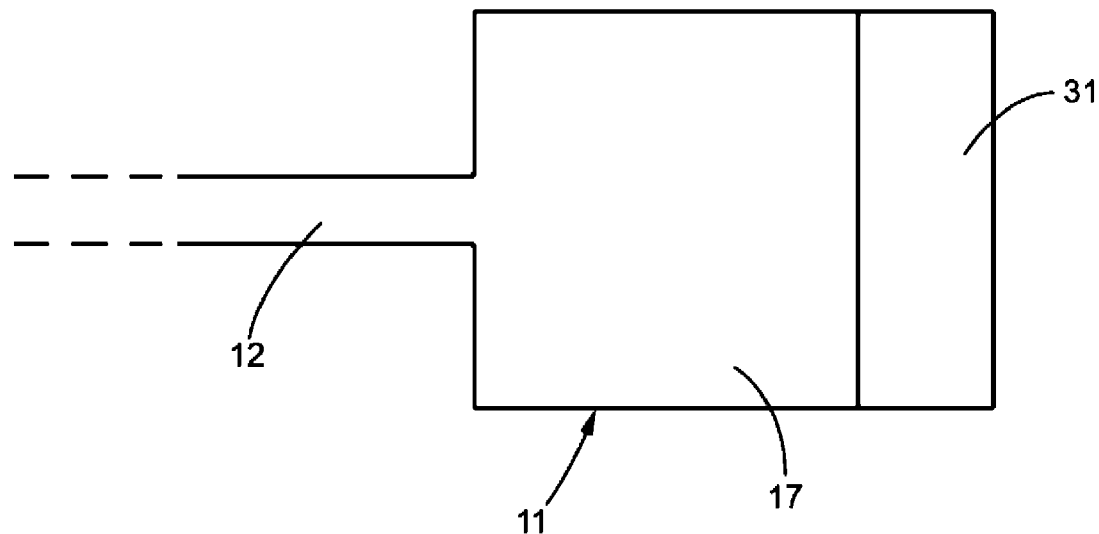

Finally, as is shown in FIG. 24, irrespective of the shape of the main portion 17, the microbalance can be supported by a single arm (for example, only the first arm 12). In this case, the movement of the single arm can be both of a torsional type and of a flexural type. There can moreover be envisaged a single appendage 31, provided, for example, on one side of the main portion 17 opposite to the single arm.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A MEMS microbalance comprising:
a semiconductor substrate having a cavity; and
a resonator suspended above the cavity of the substrate and including:

a mobile body;
a first arm coupled between the substrate and the mobile body, having a first thickness, and configured to enable oscillations of the mobile body with respect to the substrate;
an actuation transducer coupled to the mobile body and configured to generate said oscillations at a resonance frequency; and
a detection transducer configured to detect a variation in the resonance frequency,
wherein the mobile body comprises a thin portion having a second thickness smaller than said first thickness of the first arm.

2. The microbalance according to claim 1 wherein the mobile body comprises a main portion and said thin portion comprises a first appendage extending laterally from said main portion.

3. The microbalance according to claim 2 wherein the main portion has said first thickness.

4. The microbalance according to claim 2, comprising a second arm extending between said main portion and said substrate, wherein the mobile body includes a second appendage, said first and second arms delimiting a first lateral surface and a second lateral surface, opposite to one another, of said main portion; said first appendage and said second appendage extending from said first lateral surface and said second lateral surface, respectively.

5. The microbalance according to claim 4 wherein said first and second appendages have a shape chosen from among rectangular, square, crescent-shape, and T-shape.

6. The microbalance according to claim 2 wherein said first appendage comprises one or more holes.

7. The microbalance according to claim 1 wherein the mobile body has a main portion that is constituted by said thin portion and has said second thickness.

8. The microbalance according to claim 1, comprising a bond layer on said thin portion and configured to form a bond with molecules or portions of molecules.

9. The microbalance according to claim 1 wherein said resonator is a magnetic-inductive resonator, wherein the actuation transducer comprises an actuation winding provided in the mobile body in a first metal level, and wherein the detection transducer comprises a detection winding provided in the main body in a second metal level.

10. The microbalance according to claim 9, comprising a second arm extending between said mobile body and said substrate, wherein the actuation winding comprises an actuation loop made of conductive material and first connection portions, and the detection winding comprises a detection loop made of conductive material and second connection portions, said first and second connection portions extending along said first and second arms, said first connection portions forming an input port of the actuation winding and said second connection portions forming an output port of the detection winding.

11. The microbalance according to claim 10 wherein said actuation loop and said detection loop are on the first and second metal levels, respectively, and are partially set on top of one another.

12. The microbalance according to claim 10 wherein said actuation loop and said detection loop are formed on one and the same metal level and are electrically insulated from one another.

13. A system comprising:
an interface;
a microbalance that includes:
a semiconductor substrate having a cavity; and
a resonator suspended above the cavity of the substrate and including:
a mobile body;
a first arm coupled between the substrate and the mobile body, having a first thickness, and configured to enable oscillations of the mobile body with respect to the substrate;
an actuation transducer coupled to the mobile body and configured to generate said oscillations at a resonance frequency; and
a detection transducer configured to detect a variation in the resonance frequency,
wherein the mobile body comprises a thin portion having a second thickness smaller than said first thickness of the first arm;
a magnetic field generator coupled to the actuation transducer and to the detection transducer and configured to generate a magnetic field;
a signal generator coupled to the actuation transducer, and configured to generate a signal to control the microbalance; and
a processing unit, configured to process an output signal of the detection transducer.

14. The system of claim 13 wherein the mobile body comprises a main portion and said thin portion comprises a first appendage extending laterally from said main portion.

15. The system of claim 14 wherein the main portion has said first thickness.

16. The system of claim 14, comprising a second arm extending between said main portion and said substrate, wherein the mobile body includes a second appendage, said first and second arms delimiting a first lateral surface and a second lateral surface, opposite to one another, of said main portion; said first appendage and said second appendage extending from said first lateral surface and said second lateral surface, respectively.

17. A process, comprising:
forming a MEMS microbalance, the forming including:
forming a semiconductor substrate having a cavity;
forming a resonator suspended above the cavity of the substrate and including:
forming a mobile body;
forming a first arm coupled between the substrate and the body, having a first thickness and configured to enable oscillations of the mobile body with respect to the substrate;
forming an actuation transducer coupled to the body and configured to generate said oscillations at a resonance frequency; and
forming a detection transducer configured to detect a variation of the resonance frequency,
wherein forming the body comprises forming a thin portion having a second thickness smaller than said first thickness of the first arm.

18. The process according to claim 17, comprising:
forming a structural layer on the substrate;
defining simultaneously the mobile body, the first arm, and the thin portion by selectively removing portions of the structural layer; and
forming the cavity by removing said substrate underneath said mobile body and underneath said first arm.

19. The process according to claim 18, further comprising forming a bond layer on the structural layer, said bond layer being made of material designed to create a bond with molecules or portions of molecules.

20. The process according to claim 18, wherein forming the structural layer comprises:

forming a bearing layer;

forming the actuation and detection transducers on said bearing layer;

forming a first protective layer on said actuation and detection transducers;

forming first mask regions on said first protective layer;

forming a second protective layer on said first mask regions; and selectively removing said second protective layer, said first protective layer, and said bearing layer so as to define said mobile body.

21. The process according to claim 20 wherein forming the actuation and detection transducers further comprises:

depositing a first metal level and defining said first metal level so as to form actuation loops and co-planar detection loops; and depositing a second metal level, on said first metal level, and defining said second metal level so as to form a portion of a connection of said actuation loops or said detection loops at least partially in said second metal level.

22. The process according to claim 20, comprising forming second mask regions on said second protective layer, and wherein selectively removing said second protective layer, said first protective layer, and said bearing layer defines said first arm.

23. The process according to claim 20 wherein forming the actuation and detection transducers comprises depositing a first metal level, defining said first metal level so as to form first loops, depositing a third protective layer, depositing a second metal level, and defining said second metal level so as to form second loops, set on top of said first loops.

24. The process according to claim 20 wherein forming the actuation and detection transducers comprises depositing a first metal level and defining said first metal level, forming third mask regions set on top of said bearing layer, and defining a main portion of said mobile body underneath said first mask regions and side appendages underneath said third mask regions, said side appendages being of a thickness smaller than a thickness of said main portion.

* * * * *